United States Patent [19]

Anderson

[11] Patent Number: 6,013,791
[45] Date of Patent: Jan. 11, 2000

[54] PROCESS FOR THE PREPARATION OF 4-(FORMYLTHIO)-AZETIDIN-2-ONE DERIVATIVES AND PENEM DERIVATIVES

[75] Inventor: Richard Keith Anderson, East Grinstead, United Kingdom

[73] Assignee: SmithKline Beecham p.l.c., Bretford, United Kingdom

[21] Appl. No.: 09/034,920

[22] Filed: Mar. 5, 1998

Related U.S. Application Data

[63] Continuation of application No. 08/532,625, Oct. 4, 1995, abandoned, which is a continuation of application No. PCT/GB94/00660, Mar. 29, 1994.

[30] Foreign Application Priority Data

Apr. 6, 1993 [GB] United Kingdom .................. 9307201

[51] Int. Cl.$^7$ .................................................. C07D 205/09
[52] U.S. Cl. ........................................... 540/357; 540/354
[58] Field of Search ............................................. 540/357

[56] References Cited

FOREIGN PATENT DOCUMENTS

| 0 188 247 | 7/1986 | European Pat. Off. . |
| 0 232 966 | 8/1997 | European Pat. Off. . |

OTHER PUBLICATIONS

Journal of the American Chemical Society, vol. 107, No. 22, Oct. 30, 1985, Gaston<PA US pp. 6398–6399.
Journal of the Chemical Society, Chemical Communications, No. 6, Mar. 15, 1989, Letchworth GB pp. 371–373, N.F. Osborne et al.

Alpegiani, et al., "Reactivity parameters of the metal assisted 1, 2–cleavage of penicillins", *Heterocycles*, 31(4), pp. 617–628 (1990).

*Primary Examiner*—Mark L. Berch
*Attorney, Agent, or Firm*—Edward R. Gimmi; William T. King; Charles M. Kinzig

[57] ABSTRACT

A process for the preparation of a compound of formula (IVA) which process comprises subjecting a compound of formula (V), where R is an ester-forming group or carboxy-protecting group, and X and Y are hydrogen or halogen provided that at least one of X or Y is halogen, to reductive formylation.

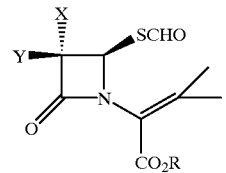

(IVA)

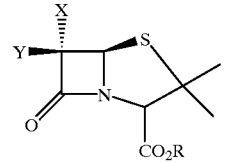

(V)

13 Claims, No Drawings

PROCESS FOR THE PREPARATION OF 4-(FORMYLTHIO)-AZETIDIN-2-ONE DERIVATIVES AND PENEM DERIVATIVES

This is a continuation of application Ser. No. 08/532,625, filed Oct. 4, 1995; which is a 371 of International Application No. PCT/GB94/00660, filed Mar. 29, 1994; which claims priority from GB Application No. 9307201.5, filed Apr. 6, 1993.

The present invention relates to a novel process useful in the manufacture of various penem derivatives.

6-(substituted methylene) penems of general formula(I):

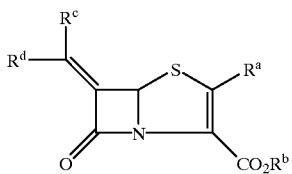

(I)

wherein $R^a$, $R^b$, $R^c$ and $R^d$ are various substituents, have been described in W087100525, EP 0 041 768 A, EP 0 120 613 A, EP 0 150 781 A, EP 0 154 132 A and EP 0 210 814 A (all Beecham).

EP 0 232 966 A, the contents of which is incorporated herein by reference thereto, describes a process for the preparation of such 6(substituted methylene)-penems, which proceeds via 6-halopenem intermediates of the general formula (II):

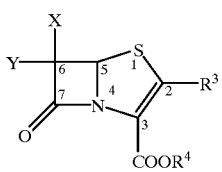

(II)

in which: X denotes a halogen atom, preferably a bromine atom; Y denotes, in one group of intermediates, a halogen atom (i.e a dihalopenem) or, preferably, a hydrogen atom, and, in a second group of intermediates, a moiety of the general formula (III):

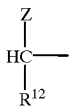

(III)

wherein: Z denotes a halogen atom, a hydroxy group, a substituted hydroxy group, an —S(O)n$R^5$ group, or an —Se (O)m$R^5$ group where $R^5$ denotes a hydrogen atom, a hydrocarbon group, or a heterocyclyl group; n denotes 0, 1 or 2, preferably 0 or 1; m denotes 0 or 1; $R^3$ denotes a hydrogen atom or an organic group; $R^4$ denotes a hydrogen atom, a carboxy-salt-forming ion, or a carboxy-ester-forming group; and $R^{12}$ denotes a hydrogen atom, an unsubstituted or substituted hydrocarbon group, or an unsubstituted or substituted heterocyclyl group, corresponding to the desired substitutent in the ultimate 6-(substituted methylene)-2-penem.

Such 6-halopenems of the general formula (II) are prepared from a 6halo- or 6,6-dihalo-penicillanic acid, via the corresponding penicillanate-1-oxide, and then via numerous alternative routes involving various intermediates to an azctidinone of the general formula (IV):

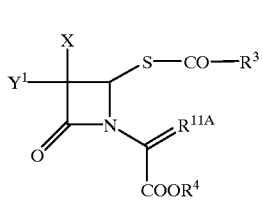

(IV)

(cf. formulae (IVA) and (VIA) in EP 0 232 966 A), in which X, $R^3$ and $R^4$ are defined as above; $Y^1$ denotes a hydrogen atom or a halogen atom; $R^{11A}$ denotes a phosphoranylidene group or an oxygen atom; and $R^4$ may alternatively denote a carboxy-protecting group Rx The azetidinone intermediate of the general formula (IV) may then be cyclised to give a 6halopenem of the general formula (II) in which Y denotes $Y^1$ as defined above The 6-halopenem of formula (II) may then be converted, for example via a 6halopenem of the general formula (II) in which Y denotes a moiety of the formula (II), to the desired 6-(substituted methylenetpenem of formula (I).

A publication in J. Am. Chem Soc. (1985), 107, 6398–6399 by Farmitalia describes the preparation of azetidinones of general formula (IV) from penicillanic acid esters without the intermediacy of the corresponding penicillanate-1-oxide. The process described therein is based on the silver assisted cleavage of the penicillanate, and an electron withdrawing carboxylate group in the 3-position of the penicillanate is essential for the reaction to produce acceptable yield values.

Consequently, when the conditions described in this publication are applied to the preparation of a compound of formula (IV), wherein the ester group is not an electron withdrawing group, very poor or negligible amounts of the compound of formula (IV) are obtained.

According to the present invention there is provided a process for the preparation of a compound of formula (IVA):

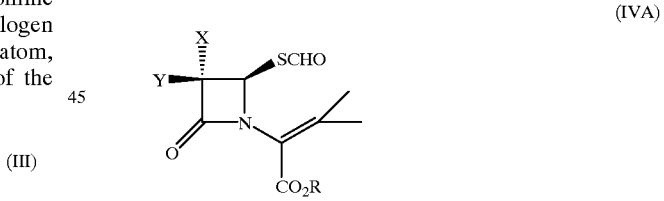

(IVA)

which process comprises subjecting a compound of formula (V):

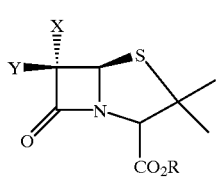

(V)

where R is an ester-forming group or carboxy-protecting group, and X and Y are hydrogen or halogen provided that at least one of X or Y is halogen, to reductive formylation.

Suitable ester-forming groups R include pharmaceutically acceptable ester-forming or in-vivo hydrolysable ester-forming groups. Suitably R may be a readily removeable carboxy protecting ester group.

The term 'halogen' includes chlorine, bromine and iodine. Preferably at least one of X or Y is bromine. Suitably X is bromine and Y is hydrogen Such compounds of formula (IVA) are primarily useful as intermediates in the preparation of β-lactam compounds, for example particularly the 6-(substituted methylene) compounds of formula (I) referred to above Suitable ester-forming carboxyl-protecting groups from which R may be selected include those which may be removed under conventional conditions. Such groups include benzyl, p-methoxybenzyl, benzoylmethyl, p-nitrohenzyl, 4-pyridylmethyl, 2,2,2-trichloroethyl, 2,2,2-tribromoethyl, t-butyl, t-amyl allyl, diphenylmethyl, triphenylmethyl, adamantyl, 2-benzyloxyphenyl, 4-methyl-thiophenyl, tetrahydrofur-2-yl, tetrahydropyran-2-yl, pentachlorophenyl, acetonyl, p-toluenesulphonylethyl, methoxymethyl, a silyl, stannyl or phosphorus- containing group, an oxime radical of formula —N=CHR$^9$ where R$^9$ is aryl or heterocyclyl.

A CO$_2$R group in which R is hydrogen may be regenerated from any of the above-mentioned esters by usual methods appropriate to the particular R group, for example, acid-, base-, or by enzymically- catalysed hydrolysis, or by hydrogenolysis under conditions wherein the remainder of the molecule is substantially unaffected. Suitable methods will be well known to those skilled in the art.

In the process of this invention the compound of formula (IVA) may be prepared from the compound of formula (V) by treating the compound of formula (V) with a silver compound, typically in the presence of a base, followed by treatment with a formulating reagent.

The silver compound may for example be silver oxide or a silver salt, of for example an inorganic or (C$_{1-10}$) alkanoic acid, such as silver acetate. The base may suitably be an organic base, preferably a non-nucleophilic strong organic base such as 1,8- diazabicyclo [5,4,0] undec-7ene ('DBU'), or 1,S-diazabicyclo[4,3,0]non-5ene ('DBN'). Typically this reaction may be carried out in the presence of a pyridine such as an alkylpyridine, for example picolines such as α-picoline, which can assist in solubilizing the base.

The reaction may be carried out in an organic solvent, for example acetone, acetonitrile, dimethylsulphoxide, dimethylformamide or dichloromethane. The reaction is preferably performed at a low temperature, suitably from +3° C. to −30° C., more suitably from 0° C. to −15° C., a reduced temperature reducing the level of impurities but slowing the reaction down. If a silver salt is used, preferably light is excluded from the reaction medium to reduce photodecomposition of the silver salt.

Suitably the silver salt and the picoline may be first reacted together in a solvent, then the base may be added, then to this mixture may then be added the compound of formula (V), and subsequently the formulating agent and sodium iodide. It is believed that the initial stage of reaction of the compound of formula (V) with the silver compound, typically in the presence of a base, yields an intermediate silver salt of formula (VA):

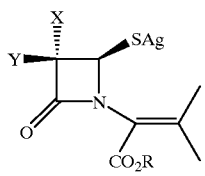

(VA)

where X and Y are as defined in formula (V), which need not be isolated, and may be handled in situ.

Optimised conditions for this initial stage of the process appear to be:

- silver acetate: ca. 1.2 equivalents (e.g ±10%)
- α-picoline: ca. 7.1 equivalents (e.g ±10%)
- DBU: ca. 1.0 equivalents (e.g ±10%)
- formula (V) compound ca. 1.0 equivalents (e.g ±10%)
- acetone solvent: ca. 33 equivalents (e.g ±10%) with the reaction being carried out at 0–3° C. for 14–16 hours.

Preferably the formylating agent is in excess relative to the compound of formula (V). A suitable formylating reagent for the process is a compound of formula (VI):

$$R^{21}\text{—CO—O—CO—H} \tag{VI}$$

in which R$^{21}$ denotes an alky, e.g (C$_{1-6}$) alkyl or aryl group. A suitable formylating reagent of formula (VI) is, for example, acetic formic anhydride ('AFA'). Acetic formic anhydride may be prepared separately and distilled into the reaction mixture, or may alternatively be prepared in situ, for example by known reactions between acetyl chloride and sodium formate, or between formic acid and acetic anhydride.

Silver may be recovered from the formylation reaction by carrying out the reaction in the presence of sodium iodide, preferably also in excess relative to the compound of formula (V), to enable recovery of silver residues by precipitation as silver iodide.

The azetidinone of formula (IVA) may then be converted to a 6-halo- or 6,6dihalo- penem of the general formula (II), in which Y denotes Y$^1$, by for example a process involving ozonolysis, phosphoranylation and cyclisation, in a known manner, for example as more particularly described in EP 0 232 966 A. The 6-halo- or 6,6-dihalo- penmen of the general formula (II) may then be used to prepare 6-(substituted methylene) penems of formula (I) of the type discussed above in a known manner, for example as more particularly described in EP 0 232 966 A. An example of a 6(substituted methylene) penem of formula (1) which may be prepared in this way is sodium (5R)-6-[(Z)-(2,3 -dihydroimidazo[2,1-b] thiazol-6-yl) methylene]penem-3-carboxylate.

The term 'aryl' as used herein denotes phenyl or naphthyl either unsubstituted or substituted by up to five, for example one, two or three optional substituents.

The terms 'heterocyclyl' and 'heterocyclic' as used herein denote aromatic and non-aromatic, single and fused, rings suitably containing up to four hetero-atoms in each ring selected from oxygen, nitrogen and sulphur, which rings may be unsubstituted or substituted by, for example, up to three groups selected from halogen, (C$_{1-6}$)alkyl, (C$_{1-6}$) alkoxy, halo(C$_{1-6}$)alkyl, hydroxy, carboxy, carboxy salts, carboxy esters such as (C$_{1-6}$)alkoxycarbonyl, (C$_{1-6}$) alkoxycarbonyl(C$_{1-6}$)alkyl, aryl, and oxo groups. Each heterocyclic ring suitably has from 4 to 7, preferably 5 or 6, ring atoms. The term 'heteroaryl' refers to an aromatic heterocyclic ring or ring system, suitably having 5 or 6 ring atoms in each ring. A fused heterocyclic ring system may include carbocyclic rings and need include only one heterocyclic ring. Compounds containing a heterocyclyl group may occur in two or more tautomeric forms depending on the nature of the heterocyclyl group; all such tautomeric forms are included within the scope of the invention.

Examples of suitable optional substituents for the above-mentioned aryl, heterocyclic and heteroaryl groups include $(C_{1-6})$alkanoyl, $(C_{1-6})$alknoyloxy, heterocyclyl, amino, $(C_{1-6})$alkanoylamino, (mono or di)-$(C_{1-6})$alkylamino, hydroxy, $(C_{1-6})$alkylsulphinyl, $(C_{1-6})$alkylsulphonyl, heterocyclylthio, arylthio, sulphamoyl, carbamoyl, amidino, guanidino, nitro, halogen, carboxy, carboxy salts, carboxy ester,arylcarbonyl and heterocyclylcarbonyl groups.

The following example will illustrate the preparation of a compound of formula (IVA) according to the process of the invention.

EXAMPLE 1

(3S,4R)3-Bromo4(formylthio)-1(1-p-methoxybenzyloxycarbonyl-2-methylprop-1-enyl)azetidin-2-one.

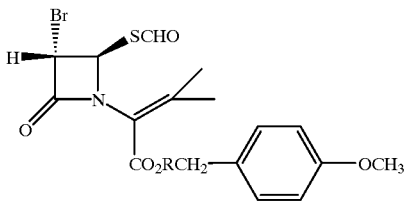

(a) A stirred suspension of silver acetate (10.0 g, 0.05 mole) in acetonitrile (100 ml) and protected from light was treated with α-picoline (35 ml) and the resultant solution cooled to 0° C. 1,8-diazabicyclo [5,4,0]undec-7-ene (9.0 ml, 0.06 moles) was added and the mixture stirred at 0–3° C. for 30 mins. A suspension of p-methoxybenzyl 6-α-bromopenicillanate (i.e formula (V)) (20.0 g, 0.05 moles) in acetonitrile was added at 0–3° C. and the reaction stirred at 3° C. for 14 hours. The product is believed to be an intermediate silver salt of formula (VA).

(b) The reaction mixture was cooled to −15° C. and treated sequentially with AFA (i.e formula (VI)) (66.0 g, 0.75 moles) and sodium iodide (37.5 g. 0.25 moles) keeping the temperature −15° C. to −12° C. The mixture was stirred at −15° C. for 10 mins. then allowed to rise to 0° C. over 30 mins during which time a thick beige suspension was formed. The suspension was diluted with toluene (500 ml) and shaken with 10% aqueous citric acid (1000 ml), filtered, and the organic phase separated and further washed with brine (2×250 ml), saturated sodium bicarbonate (250 ml), and brine (2×250 ml), dried over magnesium sulphate and evaporated. The residual yellow syrup (22.0 g) was dissolved in cold ethanol (100 ml), seeded and stored at −18° C. for 1 hour to give the title compound (i.e of formula (IVA)) as pale yellow crystals (12.8 g. 60%).

EXAMPLE 2

(a) A stirred suspension of silver acetate (100 g, 6.0 mole) in acetone (0.5 L) and protected from light was treated with α-picoline (350 ml) and the resultant solution cooled to 2° C. DBU (1,8-Diazabicyclo[5,4,0]undec-7-ene) (82 ml, 0.55 moles) was added and the mixture stirred at 2–3° C. for 35 min. A pre-cooled (3° C.) solution of p-methoxybenzyl 6-α-bromopenicillanate (V), (200 g, 0.5 moles) in acetone (0.5 L) was added over 5.0 hr. keeping the temperature between 2–4° C. and the reaction stirred at 0–2° C. for 20.5 hr.

(b) The above reaction mixture was cooled to −28° C. and treated with acetic formic anhydride (AFA) (660 g, 7.5 moles) over 10 minutes keeping the temperature—at −24±4° C. followed by a solution of sodium iodide (375 g, 2.5 moles) in acetone (2 L) over 20 min. keeping the temperature at −20±2° C. The mixture was stirred at—25° C. for 10 minutes then allowed to rise to 5° C. over 1 hr. during which time a thick beige suspension was formed. The mixture was stirred with toluene (7.5 L) and 20% aqueous citric acid (5 L), filtered and the phases of the filtration separated. The organic phase was washed with brine (2×2.5 L), saturated sodium hydrogen carbonate (2×5 L) and brine (2×4 L), dried over $MgSO_4$, filtered and evaporated to a syrup crystallising to a yellow solid (223 g), Triturating with cold propan-2-ol gave a pale yellow solid (144.7 g, 68%), with physical data consistent with the product of example 1.

EXAMPLE 3

Preparation via AFA prepared in situ

A suspension of methanol-washed and oven-dried sodium formate (7.9 g, 0.116 M) in acetone (25 ml), stirred mechanically and by sonication, was treated with acetyl chloride (7.11 ml, 0.1 M) over ca. 3 min. at 8–10° C., after which time chlorine ions were no longer detected in a sample of the supernatant liquors ($AgNO_3/HNO_3$). Sonication was stopped and the mixture cooled and kept at 20±2° C. during the sequential dropwise addition of solutions of the silver salt prepared as described in example 2(a), one hundredth scale using DBU 0.005 M (0.76 ml) over 5 min and sodium iodide (1.9 g, 0.013 M) in acetone (12 ml+3 ml washing) over 5 min. The buff suspension was stirred at −21°± for 10 min then for 30 min allowing to 0° C. Toluene (50 ml) was added and the mixture shaken with 50% aqueous brine (100 ml), filtered and the organic phase separated, washed further with brine (2×50 ml), saturated sodium bicarbonate solution (1×50 ml, 1×25 ml) and brine (1×50 ml) dried over magnesium sulphate and evaporated to a syrup then under high vacuum to a pale yellow solid. NMR indicated an activity yield ca. 63%.

EXAMPLE 4

Preparation via AFA prepared in situ.

An acetone solution of silver salt prepared as described above in Example 2(a) one hundredth scale using 0.005 M (0.76 ml) DBU was cooled and kept at −25 to 30° C. during the sequential dropwise addition of formic acid (98/100%, 1.34 ml, 0.036 M) over 2 min. and acetic anhydride (3.35 ml, 0.036 M). The dark mixture was stirred and allowed to 5° C. over 30 min, cooled to −20° C. and treated with a solution of sodium iodide (1.9 g, 0.013 M) in acetone (15 ml) over 5 min. The brown suspension was stirred and allowed to 5° C. over 30 min. Toluene (50 ml) was added and stirred for 10 min., and pale yellow suspension shaken with 50% aqueous brine (100 ml), filtered and the pale yellow organic phase futher washed with 50% aqueous brine (2×500 ml), saturated sodium bicarbonate solution (1×50 ml, 1×25 ml) and brine (1×50 ml) dried over magnesium sulphate and evaporated to a syrup then under high vacuum to a pale yellow solid (2.0 g). Trituration with propan-2-ol (10 ml) gave a white solid (1.4 g) with a very clean nmr spectrum (activity yield 65%).

I claim:

1. A process for the preparation of a compound of formula (IVA):

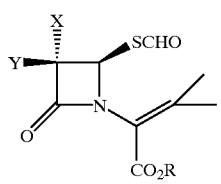

(IVA)

where R is a carboxy-protecting group, and X and Y are hydrogen or halogen provided that at least one of X or Y is halogen, which process comprises subjecting a compound of formula (V):

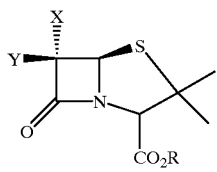

(V)

where R, X and Y are as defined above, to reductive formylation by treating the compound of formula (V) in a solvent with silver oxide or a silver salt, in the presence of a base and an alkylpyridine, followed by treatment with a formylating reagent.

2. A process according to claim 1 characterised in that X is bromine and Y is hydrogen.

3. A process according to claim 2 characterised in that the silver compound is silver oxide or a silver salt of an inorganic or $(C_{1-10})$alkanoic acid.

4. A process according to claim 3 characterised in that the silver salt is silver acetate.

5. A process according to claim 2 characterised in that the process is carried out in the presence of base.

6. A process according to claim 5 characterised in that the base is selected from the group consisting of: 1,8-diazabicyclo [5,4,0]undec-7-ene, 1,5-diazabicyclo[4,3,0]non-5-ene and an alkylpyridine.

7. A process according to claim 6 characterised in that the alkylpyridine is a-picoline.

8. A process according to claim 5 characterised in that the base is a combination of a-picoline and 1,8-diazabicyclo [5,4,0]undec-7-ene.

9. A process according to claim 1 characterised in that the formylating agent is a compound of formula (VI):

$$R^{21} - CO - O - CO - H \qquad (VI)$$

in which $R^{21}$ denotes an alkyl or aryl group.

10. A process according to claim 9 characterised in that the formylating reagent of formula (VI) is acetic formic anhydride.

11. A process according to claim 1 wherein the reaction is carried out in acetone or acetonitrile as the solvent, alone or mixed with alkylpyridine.

12. A process according to claim 2 characterised in that the reaction conditions are: silver acetate: ca. 1.2 equivalents; a-picoline: ca. 7.1 equivalents; 1,8-diazabicyclo [5,4,0]undec-7-ene: ca. 1.0 equivalents; formula (V) compound; ca. 1.0 equivalents; acetone solvent: ca. 33 equivalents.

13. A process for the preparation of a compound of formula (IVA):

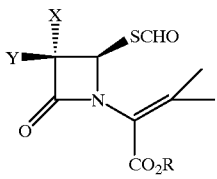

(IVA)

where R is a carboxy-protecting group, and X and Y are hydrogen or halogen provided that at least one of X or Y is halogen, which process comprises making a mixture by reacting a silver salt and alkylpyridine in a solvent followed by adding a base and then adding the compound of formula (V):

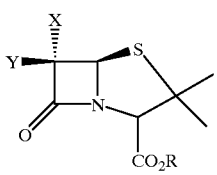

(V)

where R, X and Y are defined above, followed by treatment with a formylating agent and simultaneous or subsequent reaction with sodium iodide.

* * * * *

UNITED STATES PATENT AND TRADEMARK OFFICE
CERTIFICATE OF CORRECTION

PATENT NO. : 6,013,791
DATED : January 11, 2000
INVENTOR(S) : Richard Keith Anderson It is certified that error appears in the above-identified patent and that said Letters Patent is hereby corrected as shown below:

Column 7, line 46, change "a-picoline" to --α-picoline--.

Column 7, line 48, change "a-picoline" to --α-picoline--.

Column 8, line 14, change "a-picoline" to --α-picoline--.

Signed and Sealed this

Eighth Day of August, 2000

Attest:

Q. TODD DICKINSON

Attesting Officer

Director of Patents and Trademarks